United States Patent
Zhang et al.

(10) Patent No.: US 12,131,476 B2
(45) Date of Patent: Oct. 29, 2024

(54) SYSTEM AND METHOD FOR ESTIMATING MOTION OF TARGET INSIDE TISSUE BASED ON SURFACE DEFORMATION OF SOFT TISSUE

(71) Applicant: ZHEJIANG CANCER HOSPITAL, Zhejiang (CN)

(72) Inventors: Jie Zhang, Hangzhou (CN); Xue Bai, Hangzhou (CN); Guoping Shan, Hangzhou (CN)

(73) Assignee: ZHEJIANG CANCER HOSPITAL, Hangzhou (CN)

( * ) Notice: Subject to any disclaimer, the term of this patent is extended or adjusted under 35 U.S.C. 154(b) by 431 days.

(21) Appl. No.: 17/571,562

(22) Filed: Jan. 10, 2022

(65) Prior Publication Data

US 2022/0130048 A1    Apr. 28, 2022

Related U.S. Application Data

(63) Continuation of application No. PCT/CN2021/080052, filed on Mar. 10, 2021.

(30) Foreign Application Priority Data

Oct. 19, 2020    (CN) .......................... 202011118867.9

(51) Int. Cl.
    *G06T 7/00*    (2017.01)
    *A61B 5/06*    (2006.01)
    (Continued)

(52) U.S. Cl.
    CPC ............ *G06T 7/0016* (2013.01); *A61B 5/066* (2013.01); *G06N 3/045* (2023.01); *G06T 7/248* (2017.01);
    (Continued)

(58) Field of Classification Search
    CPC ....... G06T 7/00; G06T 7/0012; G06T 7/0014; G06T 7/0016; G06T 7/10; G06T 7/246;
    (Continued)

(56) References Cited

U.S. PATENT DOCUMENTS

| | | | |
|---|---|---|---|
| 2017/0109871 A1* | 4/2017 | Nakano | G06T 7/11 |
| 2018/0005391 A1* | 1/2018 | Miga | G06T 7/33 |

(Continued)

FOREIGN PATENT DOCUMENTS

| | | |
|---|---|---|
| CN | 102949240 A | 3/2013 |
| CN | 103295234 A | 9/2013 |

(Continued)

OTHER PUBLICATIONS

International Search Report (PCT/CN2021/080052); Date of Mailing: Jul. 19, 2021.

*Primary Examiner* — Edward F Urban
*Assistant Examiner* — Duy Tran
(74) *Attorney, Agent, or Firm* — W&G Law Group (57) ABSTRACT

Provided is a system and method for estimating the motion of a target inside a tissue based on surface deformation of the soft tissue. The system consists of an acquisition unit, a reference input unit, two surface extraction units, a target position extraction unit, a feature calculation unit, and a target motion estimation unit. The method includes: the acquisition unit acquires an image $I_i$ of the soft tissue; the surface extraction unit extracts a surface $f_i$ of the soft tissue from $I_i$; the reference input unit acquires a reference image $I_{ref}$ of the soft tissue; the surface extraction unit and the target position extraction unit respectively extract a reference surface $f_{ref}$ of the soft tissue and a target reference position $t_{ref}$ from $I_{ref}$, the feature calculation unit calculates (Continued)

deformation feature $\Psi_i$ of $f_i$ relative to $f_{ref}$, the target motion estimation unit estimates the target displacement based on $\Psi_i$ and $t_{ref}$.

9 Claims, 4 Drawing Sheets

(51) Int. Cl.
*G06N 3/04* (2023.01)
*G06N 3/045* (2023.01)
*G06T 7/246* (2017.01)
*G06V 10/75* (2022.01)
*G16H 40/60* (2018.01)

(52) U.S. Cl.
CPC .......... *G06V 10/754* (2022.01); *G16H 40/60* (2018.01); *G06T 2207/10136* (2013.01); *G06T 2207/20081* (2013.01); *G06T 2207/20084* (2013.01); *G06T 2207/30004* (2013.01)

(58) Field of Classification Search
CPC ......... G06T 7/248; G06T 7/251; G06T 7/254; G06T 2207/10136; G06T 2207/20081; G06T 2207/20084; G06T 2207/30004; G16H 40/60; G16H 30/00; G16H 30/20; G16H 30/40; G06V 10/75; G06V 10/751; G06V 10/754; G06V 10/44; G06V 2201/03; G06V 10/20; G06V 10/22; G06N 3/045; G06N 3/0455; A61B 5/066; A61B 5/7425; A61B 6/486; A61B 6/5211; A61B 8/52; A61B 8/5223; A61B 2576/00

See application file for complete search history.

(56) References Cited

U.S. PATENT DOCUMENTS

| | | | |
|---|---|---|---|
| 2019/0057505 A1* | 2/2019 | Pheiffer | G06T 7/0016 |
| 2019/0057517 A1* | 2/2019 | Koizumi | A61B 8/5215 |
| 2019/0325572 A1* | 10/2019 | Mansi | A61B 5/103 |
| 2020/0146635 A1* | 5/2020 | Wang | G06T 7/38 |
| 2020/0219272 A1 | 7/2020 | Pizer et al. | |

FOREIGN PATENT DOCUMENTS

| | | |
|---|---|---|
| CN | 103530884 A | 1/2014 |
| CN | 104318553 A | 1/2015 |
| CN | 112330603 A | 2/2021 |

* cited by examiner

SYSTEM AND METHOD FOR ESTIMATING MOTION OF TARGET INSIDE TISSUE BASED ON SURFACE DEFORMATION OF SOFT TISSUE

CROSS-REFERENCE TO RELATED APPLICATIONS

The present application is a continuation of International Application No. PCT/CN2021/080052, filed on Mar. 10, 2021, which claims priority to Chinese Application No.202011118867.9, filed on Oct. 19, 2020, the contents of both of which are incorporated herein by reference in their entireties.

TECHNICAL FIELD

The present application relates to the field of motion estimation and, in particularly, relates to a system and method for estimating the motion of a target inside a tissue based on surface deformation of the soft tissue.

BACKGROUND

Target motion estimation is an important research direction in the field of medical image processing. In a medical image, a target in a soft tissue easily moves autonomously due to respiration or changes in position due to the influence of organ displacement and deformation. In clinical applications such as needle biopsy and real-time tracking radiotherapy, risks are brought to treatment accuracy; and in the imaging field, edge blur or artifacts of a target area may be caused. Therefore, the estimation on a motion signal of a target has a significant application value. In a clinical application environment, the uncertainty of the treatment can be reduced; and in the field of fast imaging, the method is conducive to removing the artifact or blurring phenomenon from the target area.

A traditional method for performing motion estimation on a target in a soft tissue is a technical solution based on registration, and the core thereof is to obtain an optimal deformation vector field to describe the displacement of each voxel in the soft tissue, so as to estimate the displacement of the target. The method can specifically include a deformation registration method based on gray scale and a deformation registration method combined with a biomechanical model.

The deformation registration based method is based on a three-dimension (three-dimension, 3D) image (denoted as $V_0$). During the motion estimation process, a two-dimension (two-dimension, 2D) projection image (denoted as $I_p$) of the target tissue is acquired quickly by using the X-ray imaging technology. With $I_p$ as a reference, a new 3D image (denoted as $V_1$) is generated by deforming $V_0$, until the projection image $I_1$ of the $V_1$ is optimally matched with $I_p$, and the corresponding $V_1$ contains the motion displacement information of the target. The "optimal matching" in the method is usually based on the measurement criterion of image gray scale, which is easily affected by gray scale changes and noise. The time taken by the optimization iteration process required for registration also typically limits the rapidity of motion estimation. The registration combined with the biomechanical model is to integrate the knowledge of morphology, material analysis, tissue elasticity of an anatomical structure and the like into the registration process, the boundary condition limitation of registration is added, the registration accuracy is improved, and it is difficult to accurately describe the biomechanical characteristics of the anatomical structure during this process.

SUMMARY

The technical problem to be solved by the present application is to overcome the shortcomings of the prior art and provide a system for estimating the motion of a target inside a tissue based on surface deformation of the soft tissue. The system includes: an acquisition unit, a reference input unit, two surface extraction units, a target position extraction unit, a feature calculation unit, and a target motion estimation unit.

The acquisition unit is used for obtaining an actually captured image of the soft tissue; the reference input unit is used for inputting a reference image of the soft tissue; the surface extraction units are used for extracting soft tissue surfaces from the actually captured image and the reference image of the soft tissue; the target position extraction unit is used for extracting a reference position of the target from the reference image of the soft tissue; the feature calculation unit is used for calculating a deformation feature of the surface of the soft tissue in the actually captured image relative to the surface in the reference image; and the target motion estimation unit is used for calculating and outputting motion displacement estimation of the target based on the deformation feature and the reference position of the target.

Another object of the present application is to provide a method for estimating the motion of a target inside a tissue based on surface deformation of the soft tissue, which is achieved through the following steps:

S1: a reference input unit uses medical imaging equipment to capture a soft tissue image as a reference image $I_{ref}$.

In at least one embodiment of the present application, the "medical imaging equipment" includes: computed tomography (computed tomography, CT), cone-beam computed tomography (cone-beam computed tomography, CBCT), and ultrasonography.

In at least one embodiment of the present application, before the image is captured, one or more markers are implanted into a target area, and then the soft tissue image is captured by using the medical imaging equipment.

S2: a target position extraction unit identifies, calculates and outputs a reference position (denoted as $t_{ref}$) of the target from $I_{ref}$.

S3: a surface extraction unit extracts a soft tissue surface (denoted $f_{ref}$) from $I_{ref}$.

In at least one embodiment of the present application, the method of "extracting the soft tissue surface" includes: an automatic edge recognition algorithm based on adaptive threshold segmentation or a fully convolutional neural network model.

S4: an acquisition unit uses medical imaging equipment to capture an actually captured image (denoted as $I_i$) of the soft tissue.

In at least one embodiment of the present application, the "medical imaging equipment" includes: CT, CBCT, and ultrasonography.

S5: the surface extraction unit extracts a soft tissue surface (denoted as $f_i$) from $I_i$.

S6: a feature calculation unit calculates and outputs a deformation feature (denoted as $\Psi_i$) of $f_i$ relative to $f_{ref}$.

In at least one embodiment of the present application, the method of "calculating and outputting the deformation feature of $f_i$ relative to $f_{ref}$" is: inputting $f_i$ and $f_{ref}$ into $\tilde{N}$ neural network models $M=\{M_j|j=1, \ldots, \tilde{N}\}$, and the output results of the $\tilde{N}$ models together constitute the deformation feature $\Psi_i=\{\Psi_{i,j}|j=1, \ldots, \tilde{N}\}$.

S7: $\Psi_i$ and $t_{ref}$ are input into a target motion estimation unit, and a target motion estimation model (m) in the unit calculates and outputs motion estimation (denoted as $\hat{t}_i$) of the target based on $\Psi_i$ and $t_{ref}$.

The design method of the "$\tilde{N}$ neural network models $M=\{M_j|j=1, \ldots, \tilde{N}\}$" in the "feature calculation unit" in the step S6 is as follows.

(1) Modeling: establishing a fully convolutional neural network model (denoted as FCN), wherein an input layer of FCN is 2 pieces of surface data, the hidden layers include $\{l_1, \ldots l_{N-1}\}$, and an output layer is $l_N$. A deformation vector field (denoted as $\phi_k$) of the 2 pieces of surface data is output by $l_N$.

(2) Collecting training data: using medical imaging equipment to collect multiple groups of soft tissue images $I_k$, extracting changing surfaces $f_k$ (k=1, 2, \ldots, n) of the soft tissue from $I_k$, taking any one of the surfaces $\{f_k|k=1, \ldots, n\}$ as a reference surface (denoted as $f_{ref}$), and taking the rest surfaces as changing surfaces to form training sample pairs $\{(f_k, f_{ref})|k=1, \ldots, n \text{ and } k\approx ref\}$ together.

In at least one embodiment of the present application, the "medical imaging equipment" includes four-dimension (four-dimension, 4D) CT, 4D CBCT, and three-dimension ultrasonography. The soft tissue surface is directly delineated or identified by using automatic threshold segmentation or the neural network from the collected images.

(3) Training and optimizing FCN: inputting $\{(f_k, f_{ref})|k=1, \ldots, n \text{ and } k\approx ref\}$ into FCN, performing iterative optimization on the model by using unsupervised learning, setting a loss function as the difference between $f_k$ and a generated surface. The generated surface ($\phi_k \cdot f_{ref}$) is achieved by applying $\phi_k$ on $f_{ref}$, and when the loss function is optimal, terminating the optimization.

In at least one embodiment of the present application, the index for measuring the difference between $\phi_k \cdot f_{ref}$ and $f_k$ is the sum of minimum distances from all points in $\phi_k 19 f_{ref}$ to $f_k$.

(4) Constructing $M=\{M_j|j=1, \ldots, \tilde{N}\}$: in the layer structure $\{l_1, \ldots l_N\}$ of the trained FCN, and taking $\tilde{N}$ layers ($\{l_{k_j}|j=1,2, \ldots, \tilde{N}, k_j \in [1,N], \tilde{N} \le N\}$) as the output layers of $\tilde{N}$ $M_j$s respectively, wherein the input layer is consistent with that of FCN, both of which are 2 pieces of surface data, and the hidden layers of each $M_j$ is formed by sequentially ordering $\{l_1, \ldots, l_{k_j}^{-1}\}$.

If $k_j=1$, then $M_j$ is only composed of an input layer and an output layer ($l_1$).

In at least one embodiment of the present application, the "$\{l_{k_j}|j=1,2, \ldots, \tilde{N}, k_j \in [1, N], \tilde{N} \le N\}$" are preferably convolutional layers in the trained FCN, this is because the convolutional layer is a feature extraction layer in the neural network model. However, those skilled in the art can think of without creative work that other layers in the FCN except the convolutional layer can be included in the constructed model M, so as to increase the number of neural network models (M) in the feature calculation unit that is constructed accordingly. Therefore, similar technical solutions do not exceed the protection scope of the present application.

The design method of the "target motion estimation model (m)" in the step S7 is as follows.

(1) Data collection: using medical imaging equipment to capture multiple groups of soft tissue images $I_p$, and identifying and calculating a soft tissue surface $f_p$ and a target position $t_p$ from $I_p$, wherein p=1, 2, \ldots, n'.

In at least one embodiment of the present application, the "medical imaging equipment" includes 4D CT and three-dimension ultrasonography. The soft tissue images acquired by 4D CT are 10 groups of 3D CT scans which are uniformly sampled within one breathing cycle. Each 3D CT image contains a 3D image of the soft tissue surface and the target. Or, by implanting one or more markers into the target area of the soft tissue, surface changes of the soft tissue and the displacement of the marker are captured by using the 3D ultrasonography. The soft tissue surface and the target position are directly delineated or identified by using automatic threshold segmentation or the neural network from the collected images.

(2) Calculating a deformation feature $\Psi_p$ to form training data: randomly taking a group from the collected $\{(f_p, t_p)|p=1,2, \ldots, n'\}$ as reference samples, marking the same as ($f_{ref}$, $t_{ref}$), taking the rest as change samples $\{(f_p, t_p)|p=1,2, \ldots n' \text{ and } p \ne ref\}$, and inputting $\{(f_p, f_{ref})|p=1, 2, \ldots, n' \text{ and } p \ne ref\}$ into the feature calculation unit to generate the deformation feature $\Psi_p$. The deformation feature constitutes training data $\{(\Psi_p, t_p, t_{ref})|p=1,2, \ldots, n' \text{ and } p \ne ref\}$ together with $t_p$ and $t_{ref}$.

(3) Fitting the target motion estimation model (m): input data of the model is $t_{ref}$ and $\Psi_p$, the output is the displacement estimation (denoted as $\hat{t}_p$) of the target. Through iterative optimization, the difference between $\hat{t}_p$ output by the model and a true value $t_p$ thereof is minimized.

In at least one embodiment of the present application, the "difference between $\hat{t}_p$ output by the model and the true value $t_p$ thereof" is measured by the Euclidean distance between $\hat{t}_p$ and $t_p$.

In at least one embodiment of the present application, the "target motion estimation model (m)" includes: a neural network model, a fully convolutional neural network model, a linear model, and a support vector machine model.

The present application provides a system and method for estimating the motion of a target inside a tissue based on surface deformation of the soft tissue. The beneficial effects of the system and the method are: the displacement of the target is estimated depending on the deformation registration method in the prior art, the registration process is a process of obtaining an optimal solution through repeated calculations, and this process increases the time delay for estimating the displacement of the target; and on the other hand, the optimal solution for registration is often based on the gray scale similarity between a deformed image and a reference image, which determines that the accuracy of target displacement estimation in the prior art is affected by the gray difference, low contrast, noise and the like of the images. Different from the prior art, the solution provided by the present application is to fit the deformation feature with the displacement of the target, and does not include the process of repeated calculations, thus ensuring the timeliness of the estimation; and on the other hand, the deformation feature mentioned in the present application is only about the deformation of the soft tissue surface, unlike the prior art where the entire image is used as a registration object, the present application only focuses on the deformation of the surface profile, thus reducing the impact of the image quality on the accuracy. Therefore, the present application can guarantee the accuracy and the timeliness of target displacement estimation at the same time, and has a significant advantage compared with the prior art.

DESCRIPTION OF EMBODIMENTS

The present application will be further explained in conjunction with the drawings and examples.

Example 1

Figure 1:
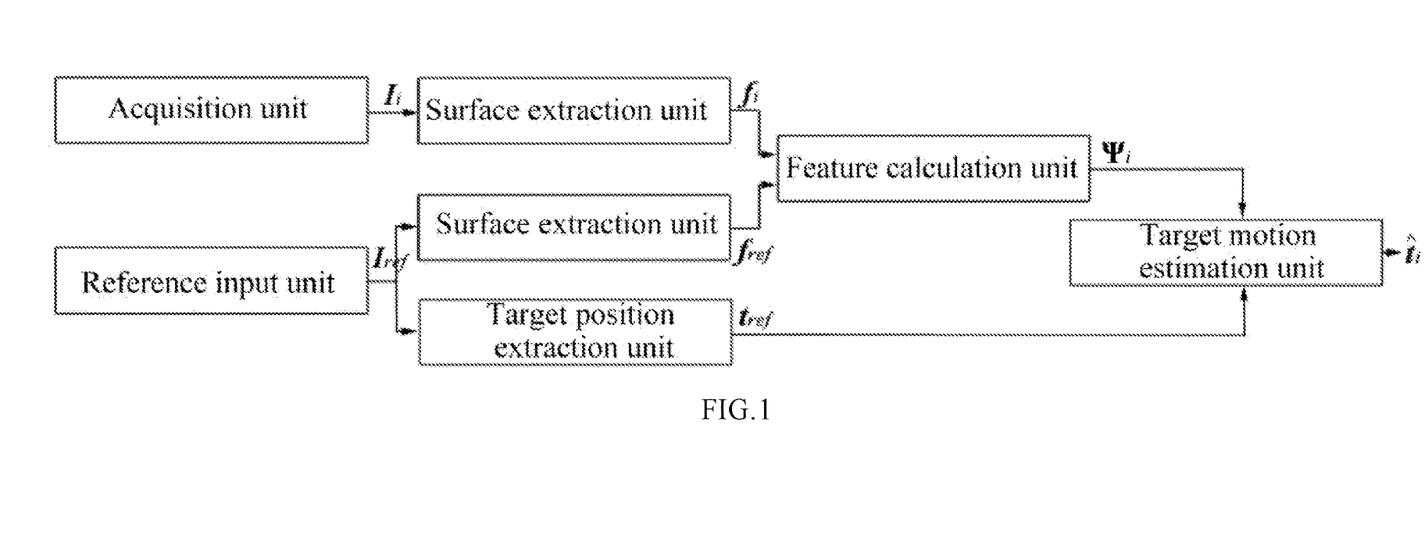
FIG. 1 is a schematic diagram of a system for estimating the motion of a target inside a tissue based on surface deformation of the soft tissue.

A system for estimating the motion of a target inside a tissue based on surface deformation of the soft tissue, as shown in FIG. 1 includes: an acquisition unit, a reference input unit, two surface extraction units, a target position extraction unit, a feature calculation unit, and a target motion estimation unit, wherein the acquisition unit is used for obtaining an actually captured image $I_i$ of the soft tissue; the reference input unit is used for inputting a reference image $I_{ref}$ of the soft tissue; the surface extraction units are used for extracting soft tissue surfaces from the actually captured image $I_i$ and the reference image $I_{ref}$ of the soft tissue, and the extracted surfaces are respectively expressed as $f_i$ and $f_{ref}$; the target position extraction unit is used for extracting a reference position $t_{ref}$ of the target from the reference image $I_{ref}$ of the soft tissue; the feature calculation unit is used for calculating a deformation feature (denoted as $\Psi_i$) of the surface $f_i$ of the soft tissue in the actually captured image relative to the surface $f_{ref}$ in the reference image; and the target motion estimation unit is used for calculating and outputting motion displacement estimation $\hat{t}_i$ of the target based on the deformation feature $\Psi_i$ and the reference position $t_{ref}$ of the target.

Example 2

Figure 2:
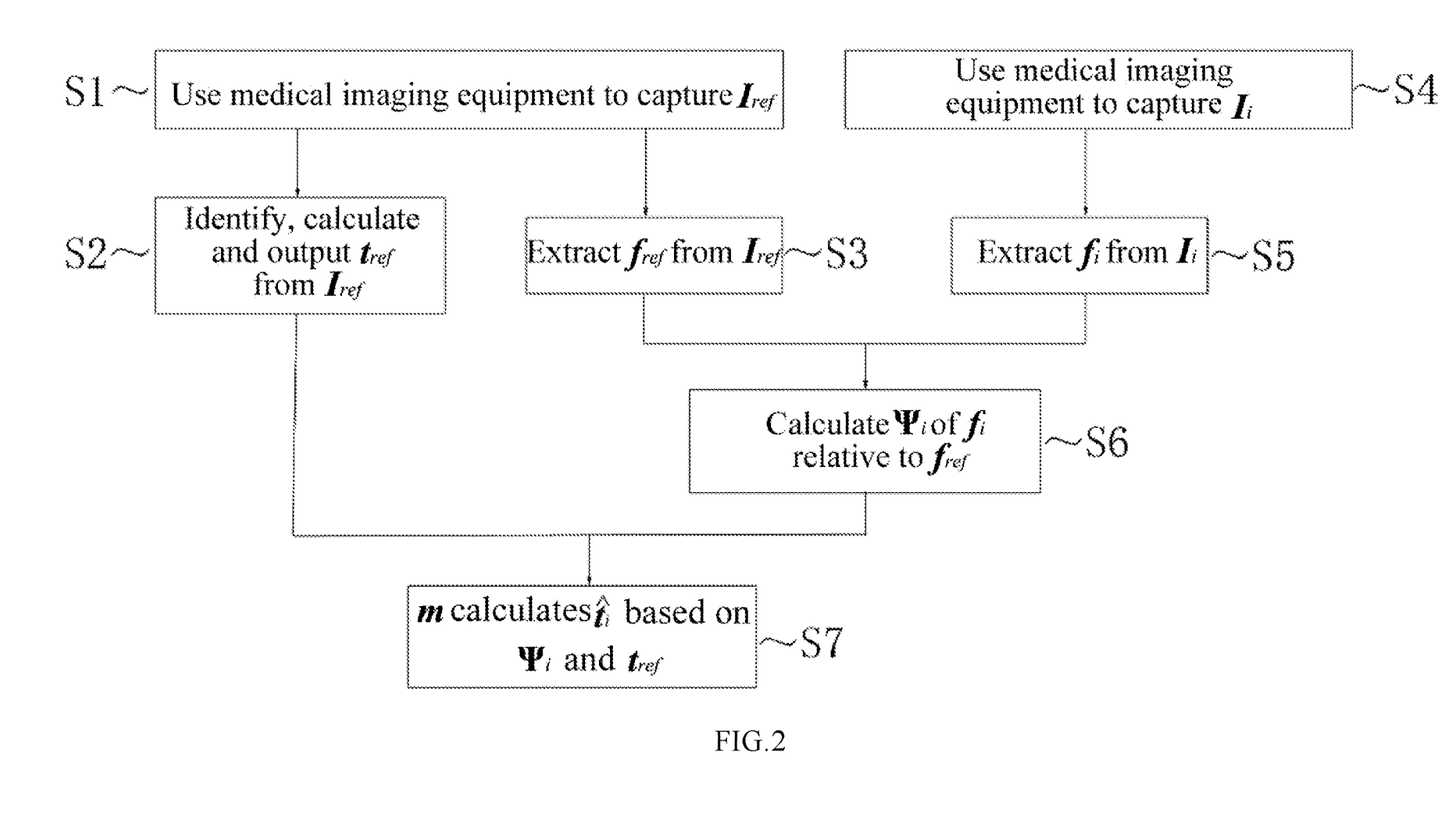
FIG. 2 is a flow diagram of a method for estimating the motion of a target inside a tissue based on surface deformation of the soft tissue.

A method for estimating the motion of a target inside a tissue based on surface deformation of the soft tissue, as shown in FIG. 2, is achieved through the following steps:

S1: a reference input unit uses medical imaging equipment to capture a soft tissue image as a reference image $I_{ref}$.

In at least one embodiment of the present application, the "medical imaging equipment" includes: CT, CBCT and ultrasonography.

In at least one embodiment of the present application, before the image is captured, one or more markers are implanted into a target area, and then the soft tissue image is captured by using the medical imaging equipment.

S2: a target position extraction unit identifies, calculates and outputs a reference position (denoted as $t_{ref}$) of the target from $I_{ref}$.

S3: a surface extraction unit extracts a soft tissue surface (denoted as $f_{ref}$) from $I_{ref}$.

In at least one embodiment of the present application, the method of "extracting the soft tissue surface" includes: an automatic edge recognition algorithm based on adaptive threshold segmentation or a fully convolutional neural network model.

S4: an acquisition unit uses medical imaging equipment to capture an actually captured image (denoted as $I_i$) of the soft tissue.

In at least one embodiment of the present application, the "medical imaging equipment" includes: CT, CBCT, and ultrasonography.

S5: the surface extraction unit extracts a soft tissue surface (denoted as $f_i$) from $I_i$.

S6: a feature calculation unit calculates and outputs a deformation feature (denoted as $\Psi_i$) of $f_i$ relative to $f_{ref}$.

In at least one embodiment of the present application, the method of "calculating and outputting the deformation feature of $f_i$ relative to $f_{ref}$" is: inputting $f_i$ and $f_{ref}$ into $\tilde{N}$ neural network models $M=\{M_j|j=1,\ldots,\tilde{N}\}$, and the output results of the $\tilde{N}$ models together constitute the deformation feature $\Psi_i=\{\Psi_{i,j}|j=1,\ldots,\tilde{N}\}$.

S7: $\Psi_i$ and $t_{ref}$ are input into a target motion estimation unit, and a target motion estimation model (m) in the unit calculates and outputs motion estimation (denoted as $\hat{t}_i$) of the target based on $\Psi_i$ and $t_{ref}$.

Figure 3:
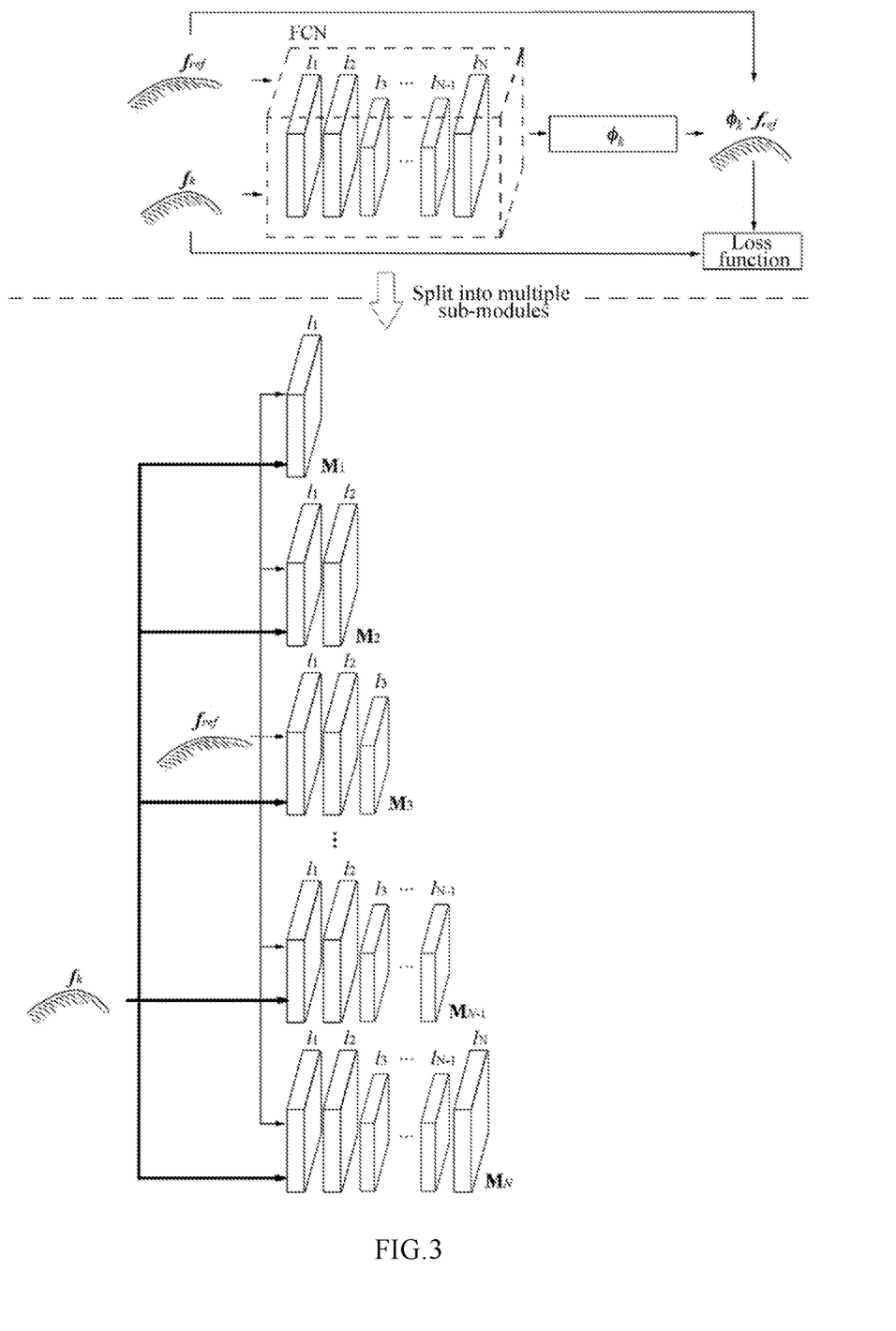
FIG. 3 is a schematic diagram of a design method of a plurality of neural network models in a feature calculation unit.

The design method of the "$\tilde{N}$ neural network models $M=\{M_j|j=1,\ldots,\tilde{N}\}$" in the "feature calculation unit" in the step S6 is:

(1) Modeling: establishing a fully convolutional neural network model (denoted as FCN), wherein an input layer of FCN is 2 pieces of surface data, the hidden layers include $\{l_1,\ldots l_{N-1}\}$ and an output layer is $l_N$. A deformation vector field $\phi_k$ of the 2 pieces of surface data is output by $l_N$.

(2) Collecting training data: using medical imaging equipment to collect multiple groups of soft tissue images $I_k$, extracting changing surfaces $f_k(k=1, 2, \ldots, n)$ of the soft tissue from $I_k$, taking any one of the surfaces $\{f_k|k=1,\ldots,n\}$ as a reference surface (denoted as $f_{ref}$), and taking the rest surfaces as changing surfaces to form training sample pairs $\{(f_k, f_{ref})|k=1,\ldots,n$ and $k\neq ref\}$ together.

In at least one embodiment of the present application, the "medical imaging equipment" includes 4D CT, 4D CBCT, and three-dimensional ultrasonography. The soft tissue surface is directly delineated or identified by using automatic threshold segmentation or the neural network from the collected images.

(3) Training and optimizing FCN: in the embodiment shown in FIG. 3, inputting $\{(f_k, f_{ref})|k=1,\ldots,n$ and $k\neq ref\}$ into FCN, performing iterative optimization on the model by using unsupervised learning, setting a loss function as the difference between $f_k$ and a generated surface. The generated surface ($\phi_k \cdot f_{ref}$) is achieved by applying $\phi_k$ on $f_{ref}$, and when the loss function is optimal, terminating the optimization.

In at least one embodiment of the present application, the index for measuring the difference between $\phi_k \cdot f_{ref}$ and $f_k$ is the sum of minimum distances from all points in $\phi_k \cdot f_{ref}$ to $f_k$.

(4) Constructing $M=\{M_j|j=1,\ldots,\tilde{N}\}$: in the embodiment shown in FIG. 3, $\tilde{N}=N$, that is, all layers in the trained FCN construct N neural network models $M=\{M_j|j=1,\ldots,N\}$ The input layer of each $M_j$ is consistent with that of FCN, both of which are 2 pieces of surface data $(f_k, f_{ref})$, the output layer is $l_j$, and the hidden layers are formed by sequentially ordering $\{l_1,\ldots,l_{j-1}\}$.

If $j=1$, then $M_1$ is only composed of an input layer and an output layer $(l_i)$.

Figure 4:
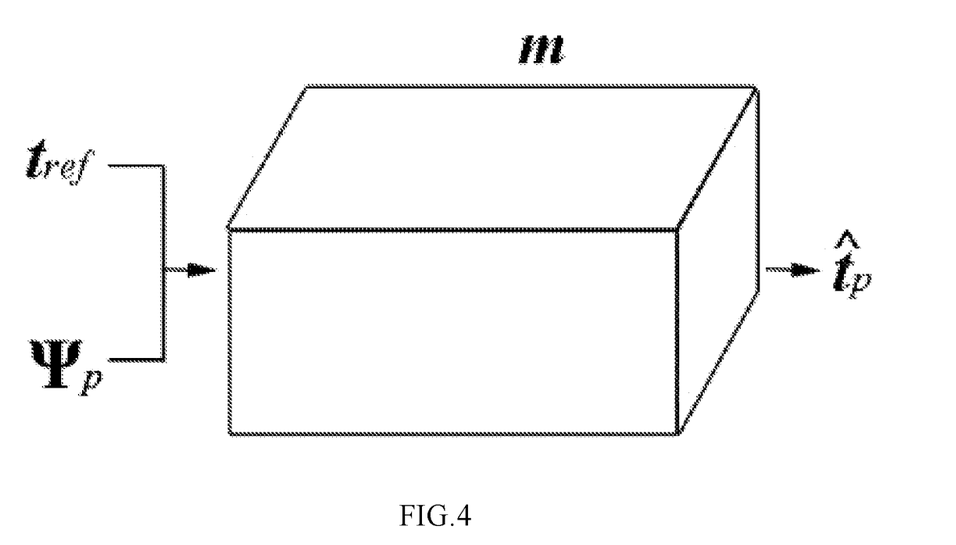
FIG. 4 is a schematic diagram of a method of a target motion estimation model.

The design method of the "target motion estimation model (m)" in the step S7 is:

(1) data collection: using medical imaging equipment to capture multiple groups of soft tissue images $I_p$, and identifying and calculating a soft tissue surface $f_p$ and a target position $t_p$ from $I_p$, wherein $p=1,2,\ldots,n'$.

In at least one embodiment of the present application, the "medical imaging equipment" includes 4D CT and three-dimensional ultrasonography. The soft tissue images acquired by 4D CT are 10 groups of 3D CT scans which are uniformly sampled within one breating cycle. Each 3D CT image contains a 3D image of the soft tissue surface and the target. Or, by implanting one or more markers into the target area of the soft tissue, surface changes of the soft tissue and the displacement of the markers are captured by using the 3D ultrasonography. The soft tissue surface and the target position are directly delineated or identified by using automatic threshold segmentation or the neural network from the collected images.

(2) Calculating a deformation feature $\Psi_p$ to form training data: randomly taking a group from the collected $\{(f_p, t_p)|p=1,2,\ldots n'\}$ as reference samples, marking the same as $(f_{ref}, t_{ref})$, taking the rest as change samples $\{(f_p,t_p)|p=1,2,\ldots,n'$ and $p\neq ref\}$, and inputting $\{(f_p,f_{ref})|p=1,2,\ldots,n'$ and $p\neq ref\}$ into the feature calculation unit to generate the deformation feature $\Psi_p$. The deformation feature constitutes training data $\{(\Psi_p, t_p, t_{ref})|p=1,2,\ldots,n'$ and $p\neq ref\}$ together with $t_p$ and $t_{ref}$.

(3) Fitting the target motion estimation model (m): in the embodiment shown in FIG. 4, the input data of the model is $t_{ref}$ and $\Psi_p$, the output is the displacement estimation (denoted as $\hat{t}_p$) of the target. Through iterative optimization, the difference between $\hat{t}_p$ output by the model and a true value $t_p$ thereof is minimized.

In at least one embodiment of the present application, the "difference between $\hat{t}_p$ output by the model and the true value $t_p$ thereof" is measured by the Euclidean distance between $\hat{t}_p$ and $t_p$.

In at least one embodiment of the present application, the "target motion estimation model (m)" includes: a neural network model, a fully convolutional neural network model, a linear model, and a support vector machine model.

The core of the technical solution of the present application for realizing target displacement estimation is fitting, that is, correlating the target displacement with the deformation feature of the soft tissue surface using a mathematical expression. Since the speed at which the mathematical expression gives an estimated value is only related to the own calculation speed of a computer, the present application can ensure the timeliness of estimation. The source of the motion of the target in the soft tissue is the deformation of the soft tissue, and the most obvious deformation is a change on its surface, therefore, in the solution provided by the present application, the feature describing the surface deformation of the soft tissue is used as an association object, and the deformation feature is extracted by reconstructing the output of the hidden layers of the neural network, the function of the neural network is to realize the matching of the actually measured surface and the reference surface, and in order to avoid the influence of the gray scale of the image, the matched object adopts a surface contour extracted from the image.

What is claimed is:

1. A system for estimating the motion of a target inside a soft tissue based on surface deformation of the issue comprising:
an acquisition unit configured to obtain an actually captured image of the soft tissue,
a reference input unit configured to input a reference image of the soft tissue,
a first surface extraction unit configured to extract soft tissue surfaces from the reference image of the soft tissue,
a second surface extraction unit configured to extract soft tissue surfaces from the actually captured image,
a target position extraction unit configured to extract a reference position of the target from the reference image of the soft tissue,
a feature calculation unit configured to calculate a deformation feature of the surface of the soft tissue in the actually captured image relative to the surface in the reference image, and
a target motion estimation unit configured to calculate and output a motion displacement estimation of the target based on the deformation feature and the reference position of the target,
wherein the acquisition unit is connected to the second surface extraction unit, the second surface extraction unit is connected to the feature calculation unit, the first surface extraction unit is connected to the reference input unit and the feature calculation unit, the reference input unit is connected to the target position extraction unit, and the target motion estimation unit is connected to the feature calculation unit and the target position extraction unit.

2. A method for estimating the motion of a target inside a soft tissue based on surface deformation of the tissue comprising the following steps:
S1: capturing, by a reference input unit, a soft tissue image as a reference image $I_{ref}$ by using medical imaging equipment;
S2: identifying, calculating and outputting, by a target position extraction unit, a reference position (denoted as $t_{ref}$) of the target from $I_{ref}$;
S3: extracting, by a first surface extraction unit, a soft tissue surface (denoted as $f_{ref}$) from $I_{ref}$, wherein a method of extracting the soft tissue surface comprises an automatic edge recognition algorithm by applying adaptive threshold segmentation or a fully convolutional neural network model;
S4: capturing, by an acquisition unit, actually captured image (denoted as $I_i$) of the soft tissue using the medical imaging equipment;
S5: extracting, by a second surface extraction unit, a soft tissue surface (denoted as $f_i$) from $I_i$;
S6: calculating and outputting, a feature calculation unit, a deformation feature (denoted as $\Psi_i$) of $f_i$ relative to $f_{ref}$;
wherein a method of calculating and outputting the deformation feature of $f_i$ relative to $f_{ref}$ includes: inputting $f_i$ and $f_{res}$ into $\tilde{N}$ neural network models $M=\{M_j|j=1,\ldots,\tilde{N}\}$, and output results of the $\hat{N}$ models together constitute the deformation feature; $\Psi_i=\{\Psi_{i,j}|j=1,\ldots,\tilde{N}\}$; and
S7: inputting $\Psi_i$ and $t_{ref}$ into a target motion estimation unit, and calculating and outputting, by a target motion estimation model (m) in the target motion estimation unit, a motion estimation (denoted as $\hat{t}_i$) of the target based on $\Psi_i$ and $t_{ref}$.

3. The method according to claim 2, wherein the medical imaging equipment in the steps S1 and S4 comprises: computed tomography (CT), cone-beam CT (CBCT), and ultrasonography, and in the step S1, before the image is captured, one or more markers are implanted into a target area, and then the soft tissue image is captured by using the medical imaging equipment.

4. The method according to claim 2, wherein a design method of the $\tilde{N}$ neural network models $M=\{M_j|j=1,\ldots,\tilde{N}\}$ in the feature calculation unit in the step S6 is:
(1) modeling: establishing a fully convolutional neural network model (denoted as FCN), wherein an input layer of FCN is 2 pieces of surface data, hidden layers comprise $\{l_1, \ldots, l_{N-1}\}$, and an output layer is $l_N$; and a deformation vector field (denoted as $\phi_k$) of the 2 pieces of surface data is output by $l_N$;

(2) collecting training data: using the medical imaging equipment to collect multiple groups of soft tissue images $I_k$, extracting changing surfaces $f_k$ (k=1, 2, . . . , n) of the soft tissue from $I_k$, taking any one of the surfaces $\{f_k|k=1, \ldots, n\}$ as a reference surface (denoted as $f_{ref}$), and taking the rest surfaces as changing surfaces to form training sample pairs $\{(f_k, f_{ref})|k=1, \ldots, n \text{ and } k \neq ref\}$ together;

(3) training and optimizing FCN: inputting $\{(f_k, f_{ref})|k=1, \ldots, n \text{ and } k \neq ref\}$ into FCN, performing iterative optimization on the model by using unsupervised learning, setting a loss function as the difference between $f_k$ and a generated surface achieved by applying $\phi_k$ on $f_{ref}$, and when the loss function is optimal, terminating the optimization; wherein an index for measuring the difference between $\phi_k \cdot f_{ref}$ and $f_k$ is a sum of minimum distances from all points in $\phi_k \cdot f_{ref}$ to $f_k$;

(4) constructing $M=\{M_j|j=1, \ldots, \tilde{N}\}$: in the layer structure $\{l_1, \ldots, l_N\}$ of the trained FCN, and taking $\tilde{N}$ layers $(\{l_{k_j}|j=1,2, \ldots, \tilde{N}, k_j \in [1, N], \tilde{N} \leq N\})$ as the output layers of $\tilde{N}$ $M_j$s, respectively, wherein the input layer is consistent with that of FCN, both of which are two pieces of surface data, and the hidden layers of each $M_j$ is formed by sequentially ordering $\{l_1, \ldots, l_{k_j-1}\}$.

5. The method according to claim 4, wherein the medical imaging equipment in the step (2) comprises four-dimension (4D) CT, 4D CBCT, and three-dimensional ultrasonography, and the soft tissue surface is directly delineated or identified by using automatic threshold segmentation or the neural network from the collected images.

6. The method according to claim 4, wherein in the step (4), if $k_j=1$, then $M_j$ is only composed of an input layer and an output layer ($l_1$), and the $\{l_{k_j}|j=1,2, \ldots, \tilde{N}, k_j \in [1, N], \tilde{N} \leq N\}$ is preferably a convolutional layer in the trained FCN.

7. The method according to claim 2, wherein a design method of the target motion estimation model (m) in the step S7 is:

(1) data collection: using medical imaging equipment to capture multiple groups of soft tissue images $I_p$, and identifying and calculating a soft tissue surface $f_p$ and a target position $t_p$ from $I_p$, where p=1, 2, . . . , n'.

(2) calculating a deformation feature $\Psi_p$ to form training data: randomly taking a group from the collected $\{(f_p, t_p)|p=1,2, \ldots, n'\}$ to serve as reference samples denoted as $(f_{ref}, t_{ref})$, taking the rest as change samples $\{(f_p, t_p)|p=1,2, \ldots, n' \text{ and } p \neq ref\}$, and inputting $\{(f_p, f_{ref})|p=1,2, \ldots, n' \text{ and } p \neq ref\}$ into the feature calculation unit to generate the deformation feature $\Psi_p$, wherein the deformation feature constitutes training data $\{(\Psi_p, t_p, t_{ref})|p=1,2, \ldots, n' \text{ and } p \neq ref\}$ together with $t_p$ and $t_{ref}$; and (3) fitting the target motion estimation model (m): the input data of the model is $t_{ref}$ and $\Psi_p$, the output is the displacement estimation (denoted as $\hat{t}_p$) of the target; through iterative optimization, a difference between $\hat{t}_p$ output by the model and a true value $t_p$ thereof is minimized, the difference between $\hat{t}_p$ output by the model and the true value $t_p$ thereof is measured by an Euclidean distance between $\hat{t}_p$ and $t_p$.

8. The method according to claim 7, wherein the medical imaging equipment in the step (1) comprises 4D CT and three-dimensional ultrasonography, the soft tissue images acquired by 4D CT are 10 groups of 3D CT scans which are uniformly sampled within one breathing cycle; each 3D CT image contains a 3D image of the soft tissue surface and the target, or, by implanting one or more markers into the target area of the soft tissue, surface changes of the soft tissue and the displacement of the markers are captured by using the 3D ultrasonography, and the soft tissue surface and the target position are directly delineated, or identified by using automatic threshold segmentation or the neural network from the collected images.

9. The method according to claim 7, wherein the target motion estimation model (m) in the step (3) comprises: a neural network model, a fully convolutional neural network model, a linear model, and a support vector machine model.

* * * * *